United States Patent [19]

Loewenthal

[11] Patent Number: 4,768,952

[45] Date of Patent: Sep. 6, 1988

[54] DENTAL PROBE

[76] Inventor: Bernard Loewenthal, 51 Heights Rd., Stratham, N.H. 03885

[21] Appl. No.: 48,876

[22] Filed: May 12, 1987

Related U.S. Application Data

[63] Continuation-in-part of Ser. No. 937,409, Dec. 3, 1986, abandoned.

[51] Int. Cl.⁴ ............................................. A61C 19/04
[52] U.S. Cl. ....................................... 433/72; 433/141
[58] Field of Search .................. 433/147, 72, 75, 141, 433/215

[56] References Cited

U.S. PATENT DOCUMENTS

| Re. 27,915 | 2/1974 | Kohl . | |
|---|---|---|---|
| 904,990 | 11/1908 | Powers . | |
| 1,586,302 | 5/1926 | Funk . | |
| 3,388,473 | 6/1968 | Loran . | |
| 3,411,723 | 11/1968 | Kohn | 433/141 |
| 3,559,292 | 2/1971 | Weissman | 433/72 |
| 3,855,705 | 12/1974 | Malmin . | |
| 4,203,223 | 5/1980 | Lautenschlager et al. | 433/141 |
| 4,340,069 | 7/1982 | Yeaple . | |
| 4,364,730 | 12/1982 | Axelsson | 433/147 |
| 4,377,381 | 3/1983 | Westman . | |
| 4,441,509 | 4/1984 | Kotsifas et al. . | |
| 4,445,857 | 5/1984 | Burst | 433/75 |
| 4,501,555 | 2/1985 | Ditchburn | 433/72 |
| 4,552,531 | 11/1985 | Martin | 433/147 |
| 4,665,621 | 5/1987 | Ackerman et al. | 433/32 |

OTHER PUBLICATIONS

"Hu-Friedy" Catalog, p. 4.

*Primary Examiner*—John J. Wilson
*Attorney, Agent, or Firm*—Foley & Lardner, Schwartz, Jeffery, Schwaab, Mack, Blumenthal & Evans

[57] ABSTRACT

A dental probe is disclosed for use in detecting periodontal disease and gingivitis. The probe includes an elongate member having a distal end with a flexible plastic tip thereon; the distal end has first portion indicating a non-diseased condition and a second portion indicating a diseased condition, the first portion being disposed between the tip of the distal end and the second portion, the second portion being disposed adjacent to the first portion. The invention also includes a method using the dental probe for diagnosing periodontal disease and gingivitis.

24 Claims, 2 Drawing Sheets

NORMAL

NORMAL

DISEASED

DENTAL PROBE

CROSS REFERENCE

This is a continuation-in-part of application Ser. No. 937,409, filed Dec. 3, 1986 now abandoned.

BACKGROUND OF THE INVENTION

1. Field of the Invention

This invention relates to a periodontal probe. In particular, this invention relates to a flexible periodontal probe having a calibrated tip for diagnosing periodontal disease and gingivitis.

2. Description of the Related Art

Periodontal disease is the most widespread disease in the world. It is basically an inflammatory disease of the gums which spreads to and destroys the supporting bone of the teeth. In time, teeth abscess or become loose and either fall out or are removed by a dentist. Fortunately, the dental profession has continually developed more effective methods to treat periodontal disease, but these treatments are dependent upon the patient seeking the appropriate party, usually a dentist.

The disease is largely silent as characterized by an absence of symptoms, much like high blood pressure. For example, there may or may not be bleeding or pus around the teeth. Advanced cases frequently cause systemic problems due to the massive amount of infection present.

The sole cause of periodontal disease is dental plaque which is a bacterial substance present in the mouth. However, due to the fact that every person has a different genetic background, some people are resistant to the disease while others are extremely prone. Additionally, the problem is enhanced by infrequent dental visits and non-diagnosis of the disease.

The periodontal probe is the only significant clinical tool used for checking a person's periodontal disease status. The conventional periodontal probe is inflexible and usually made of metal and available only to dentists for professional use. These conventional probes have either lines or marks to indicate the depth that the probe penetrates between the tooth and the gum. A non-diseased condition is reflected by a probe depth of from 1 to 3 millimeters between the tooth and gum. A deeper insertion indicates a problem and the depth of the insertion corresponds to the amount of bone loss.

Because of the inflexibility of the standard metal probe, the tip cannot bend. Thus, the tip of the probe goes through the wall of pockets of periodontal disease, thus causing pain discomfort and inaccurate measurements. Lacking a flexible probe or tip, dentists have occasionally used pieces of gutta percha which is inserted into areas where there are tortuous channels. An x-ray is then taken since the gutta percha shows up radiographically. This procedure is obviously very tedious and exposes the patient to additional x-rays.

A primary or first stage of periodontal disease is gingivitis and is detected by eliciting any bleeding while probing. One method of diagnosis of gingivitis is the use of pieces of balsa wood which are sold, for example, by Johnson & Johnson under the trademark "STIM-U-DENT." One problem with the use of pieces of balsa wood is that they are too large and rough to be used accurately.

Thus, it has been difficult or impossible to reach into periodontal pockets because they are tortuous, and the metal probes can only go in a straight line and may not penetrate the full depth of the pocket.

Further, back teeth have two or more roots. Frequently, bone is lost during periodontal disease between the roots. This area of the tooth where the roots divide is referred to as the "furcation". When bone is lost between roots, there exists a "furcation involvement." The depth of furcation involvement is of paramount importance in determining the prognosis and treatment of the tooth. Without a means of properly penetrating these areas, it is difficult or impossible to make a proper diagnosis.

A majority of dentists do not routinely probe for periodontal disease. In addition to the lack of routine examination by the dental profession, most physicians are not even aware of the problem.

The dental instrument art lacks a probe that the consumer can use to self-diagnose periodontal disease and gingivitis. The medical profession also lacks a disposable, easy-to-use dental probe for detecting periodontal disease and gingivitis. A method for routinely diagnosing and monitoring periodontal disease and gingivitis by persons other than a dentist does not currently exist.

SUMMARY OF THE INVENTION

It is therefore an object of the present invention to provide a dental probe useful for the early detection of periodontal disease and gingivitis.

It is also an object of the present invention to provide a dental probe that allows for inexpensive self-testing at home.

It is a further object of the present invention to provide an opportunity to educate the user about periodontal disease.

Another object of the invention is to provide a flexible periodontal probe which can "snake" its way around tortuous pockets and give a more reliable diagnosis of periodontal disease.

A further object is to provide a flexible dental probe which is able to bend and not pierce the wall of pockets caused by the disease.

Yet another object of the invention is to provide a dental probe for detecting gingivitis by means of the flexible tip. Specifically, the instant flexible tip dental probe is more flexible and accurate in reaching into periodontal pockets since it has the ability to go around corners in tortuous pockets, thus giving more accurate results.

Another object is to detect furcation involvement by means of a flexible tip probe which has the ability to flex and bend, thus enabling the examiner to probe furcations in a manner not previously possible, specifically because conventional probes are normally not able to negotiate furcations.

Another object is to provide a flexible rounded tip probe which is more comfortable to use than conventional rigid probes. The flexible tip of the instant invention does not penetrate the wall of the pocket formed by gum tissue as is the case with the rigid conventional probe. This eliminates much of the pain since it bends, making the examination more comfortable.

Another object of the invention is for research purposes in demonstrating the position of the tip of the periodontal probe when in use which could not previously be done because the metal probe could not be cut along with the bone and gum tissue due to its hardness.

Yet another object is the diagnosis of gingivitis by demonstrating the bleeding point.

Still another object of the invention is the use of a flexible plastic probe in determining the periodontal status around titanium screw implants. This is because it is recommended that such implants not be touched by metal or anything that could scratch them. Any scratches on implants will attract plaque and may affect the prognosis.

Another object of the invention is to provide an easy, disposable dental probe for the use of physicians to routinely check for periodontal disease.

It is still another object of the invention to provide a method for the detection of periodontal disease.

Yet another object of the invention is to provide a reusable dental probe for the detection of periodontal disease that does not require a visit to the dentist unless a problem is indicated by the use of the dental probe.

In accordance with one aspect of the present invention these objects are achieved by a flexible tip plastic dental probe, comprising:
- an elongated member having a distal end with a flexible tip thereon;
- the distal end comprising a first portion indicating a non-diseased condition and a second portion indicating a diseased condition;
- wherein the first portion is disposed between the tip of the distal end and the second portion, and the second portion is disposed adjacent to the first portion.

In accordance with another aspect of the present invention these objects are achieved by a method for diagnosing periodontal disease comprising the steps of:
(a) retracting the lip of a person to be diagnosed;
(b) gently inserting a dental probe, at the juncture between a tooth and gum, comprising:
- an elongated member having a distal end with a tip thereon;
- the distal end comprising a first portion indicating a non-diseased condition and the second portion indicating a diseased condition;
- wherein the first portion is disposed between the tip of the distal end and the second portion, and the second portion is disposed adjacent to the first portion;
(c) examining the distal end and ascertaining which of the two portions is visible at the juncture;
(d) removing the dental probe from between the tooth and gum; and
(e) repeating steps (b) through (d) at least once.

BRIEF DESCRIPTION OF THE DRAWINGS

Other objects, features and advantages of the present invention will become apparent from the following detailed description and accompanying drawings wherein.

DETAILED DESCRIPTION OF THE PREFERRED EMBODIMENTS

Figure 1:
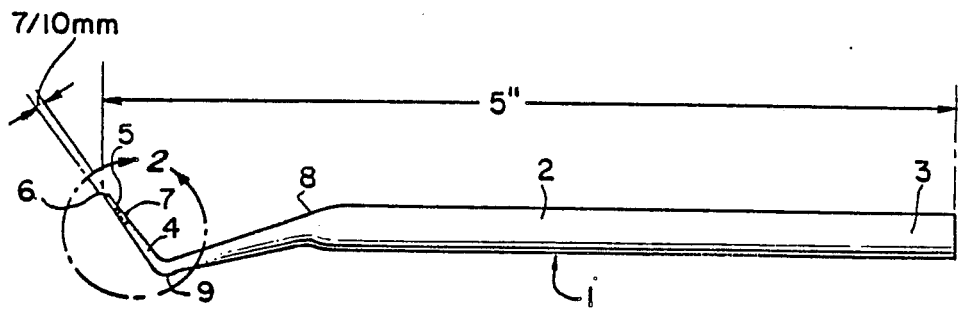
FIG. 1 is a side plan view of a dental probe.

Referring to FIG. 1, there is shown a dental probe 1 comprising an elongated member 2. The elongated member 2, which is of FDA approved non-toxic plastic material for oral use, such as 40% talcum filled polypropylene or polybutylene terephthalate, has a proximal end 3 and a distal end 4. The distal end 4, which is flexible, has a first portion 5, indicating a non-diseased condition, which is disposed between a tip 6 and a second portion 7. The second portion 7 indicates a diseased condition and is disposed adjacent to the first portion 5.

The elongated member 2 has a first bend 8 disposed between the proximal end 3 and the distal end 4. A second bend 9 is disposed between the tip 6 and the first bend 8. It should be noted that the elongated member can have any number of bends at any desired angle which can achieve the desired function of enabling the dental probe to be held by hand and enabling the easy insertion of the distal end at the juncture between a tooth and gum. The purpose of the bends in the elongated member is to offset the distal end at an angle which facilitates easy insertion and examination of the dental probe. A desired embodiment is achieved when the first bend is directed downward forming an obtuse angle at the bottom side of the elongated member and the second bend is directed upward forming an obtuse angle at the top side of the elongated member.

Figure 2:
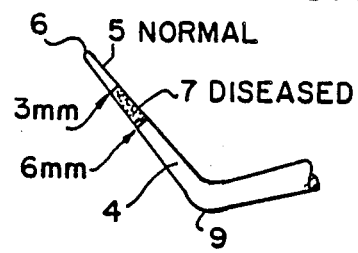
FIG. 2 is a magnified view of a section of the distal end of the dental probe shown in Figure.

Referring to FIG. 2 there is shown a magnified view of a section of the flexible distal end of the dental probe shown in FIG. 1 in which the first portion 5 is about 3 millimeters in length and the second portion 7 is about 3 millimeters in length, both portions together extending a length of about 6 millimeters from the tip 6. When the distal end is inserted at the juncture between a tooth and gum up to a length of about 3 millimeters, the first portion remains visible indicating a non-diseased condition. Insertion of the distal end beyond about 3 millimeters results in the second portion only being visible indicating a diseased condition. FIG. 2 shows the second portion extending from about the 3 millimeter mark to about the 6 millimeter mark; in a further embodiment the second portion can extend beyond about the 6 millimeter mark due to the fact that any insertion over about 3 millimeters indicates a diseased condition.

Additionally, the first and second portions can be contrastingly color-coded to aid the user when attempting to ascertain which of the two portions is visible during the examination. In one example of color-coding, the first portion can be colored green and the second portion can be colored red. In effect, any two colors which contrast each other can be chosen. The color is obtained by use of an FDA approved non-toxic ink.

The dental probe shown in FIG. 1 is about 5 inches in length, but can be any length that is convenient for hand-held use. The dental probe shown in FIG. 2 tapers from the first bend 8 to the tip 6 which has a width of about 7/10 of a millimeter. The tip at the distal end can have any width that is suitable for inserting the distal end at the juncture between a tooth and gum. The probe is flexible or bendable from point 9 to tip 6 in order to achieve the objects discussed above.

The proximal end 3 of the elongated member 2 shown in FIG. 2 has a tubular or cylindrical shape, but can be any shape which can be conveniently held by the user. For example, the cross-section of the elongated member can have a triangular, square, hexagonal or other shape.

The present invention also includes a method for diagnosing periodontal disease. This method includes the steps of retracting the lip, cheek and or tongue of a person to be diagnosed and gently inserting a dental probe at the junction between a tooth and gum. The distal end is then examined to ascertain which of the two portions is visible at the juncture and ultimately whether a diseased or non-diseased condition exists. This method creates a simple yes-no situation. The dental probe is then removed from between the tooth and gum and gently inserted at another juncture. This process can be repeated until all the tooth pockets are examined, or until only troubled areas are examined, if desired.

Figure 3:
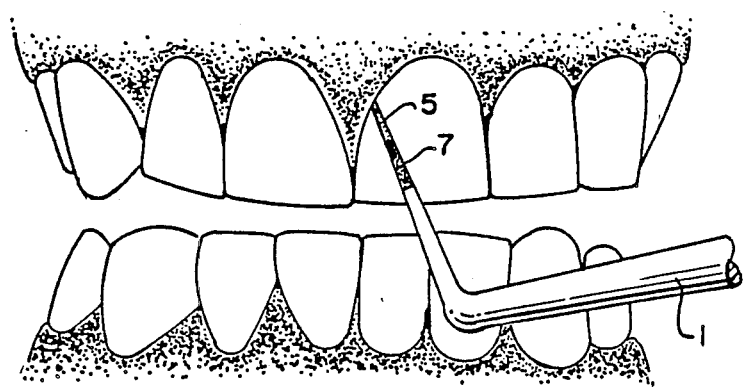
FIG. 3 is a perspective view of a dental probe inserted at the juncture between a healthy tooth and gum.

Referring to FIG. 3, there is shown the dental probe 1 inserted at a juncture between a tooth and gum. The first portion 5 remains visible indicating a non-diseased condition. The second portion 7 is also visible as a result of the dental probe not being able to penetrate at least about 3 millimeters.

Figure 4:
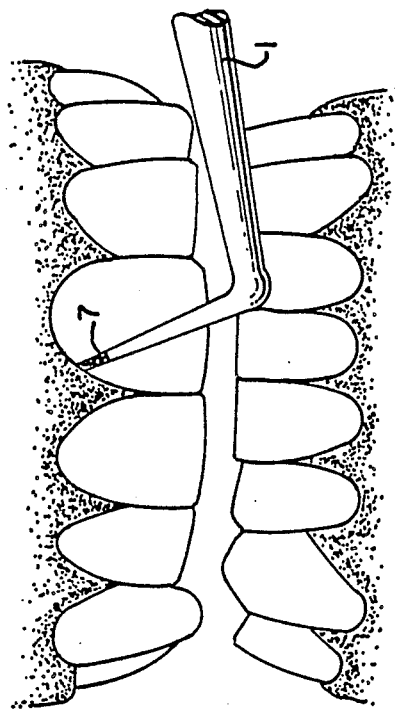
FIG. 4 is a perspective view of a dental probe inserted at the junction between a diseased tooth and gum.

Referring to FIG. 4, there is shown the dental probe 1 inserted at a juncture between a tooth and gum in which only the second portion 7 remains visible indicating a diseased condition.

The method of detecting gingivitis is substantially the same in that the probe is used to detect any bleeding. Since the tip is flexible, it can go around corners in tortuous pockets and the examiner can ascertain the full depth of the pockets. The probe can also be used to ascertain furcation involvement.

The present method can also include the step of coding the two portions with contrasting colors for ease of identification. The specific portion of the distal end visible for each tooth and gum area examined can be charted with an examination chart showing the teeth and gums in their position relative to one another. In this method, the entire mouth can be charted to determine where the troubled spots are. Additionally, the chart can be used to indicate whether or not bleeding occurred. Therefore, at a glance, the patient can see from the chart where the pockets are or where bleeding occurred. A person using this method can conceivably chart themselves after a period of time to see what changes may have occurred following either professional care or self-treatment, for example, by improved tooth brushing and dental flossing. The probe can be made from plastic and can be disposable, depending upon the desired use.

While several embodiments of the invention have been described, it will be understood that it is capable of still further modifications, and this application is intended to cover any variations, uses, or adaptations of the invention, following in general the principles of the invention and including such departures from the present disclosure as to come within knowledge or customary practice in the art to which the invention pertains, and as may be applied to the essential features hereinbefore set forth and falling within the scope of the invention or the limits of the appended claims.

What is claimed is:

1. A dental probe, comprising:
   an elongated member having a flexible, plastic distal end with a tip thereon;
   said distal end being generally cylindrical and tapered to said tip and comprising a first portion indicating a non-diseased condition and second portion indicating a diseased condition; and
   said first portion disposed between the tip of said distal end and said second portion, said second portion disposed adjacent to said first portion.

2. The dental probe according to claim 1, wherein said first portion is about 3 millimeters in length and said second portion is at least 3 millimeters in length.

3. The dental probe according to claim 1, wherein said first portion and said second portion are contrastingly color coded.

4. The dental probe according to claim 3, wherein said first portion is green and said second portion is red.

5. The dental probe according to claim 1, wherein said probe is disposable.

6. The dental probe according to claim 1, wherein said elongated member has a proximal end opposite said distal end.

7. The dental probe according to claim 6, wherein said elongated member has a first bend disposed between the proximate end and the distal end.

8. The dental probe according to claim 7, wherein said distal end has a second bend disposed between said distal end tip and said first bend.

9. The dental probe according to claim 8, wherein said first bend forms an obtuse angle at a bottom side of said elongated member.

10. The dental probe according to claim 7, wherein said second bend forms an obtuse angle at a top side of said elongated member.

11. The dental probe according to claim 1, wherein said dental probe is about 6 inches in length.

12. The dental probe according to claim 1, wherein said distal end is about 7/10 of a millimeter wide at said tip.

13. The dental probe according to claim 1, wherein at least said distal end is of plastic material.

14. The dental probe according to claim 1 wherein at least said distal end is made of an approximately 40% talcum filled plastic.

15. The dental probe according to claim 1 wherein said plastic is selected from the group consisting of polypropylene and polybutylene terephthalate.

16. A method for diagnosing periodontal disease comprising the steps of:
   (a) retracting the lip of a person to be diagnosed;
   (b) gently inserting a dental probe, at a juncture between a tooth and gum, comprising:
      an elongated member having a flexible, plastic digital end with a tip thereon;
      said distal end being generally cylindrical and tapered to the tip and comprising a first portion indicating a non-diseased condition and second portion indicating a diseased condition; and
      said first portion disposed between the tip of said distal end and said second portion, said second portion disposed adjacent to said first portion;
   (c) examining said distal end and ascertaining which of said two portions is visible at the juncture;
   (d) removing said dental probe from between the tooth and gum; and
   (e) repeating steps (b) through (d) at least once.

17. The method according to claim 16 further comprising the steps of coding said two portions with contrasting colors.

18. The method according to claim 16 further comprising the step of charting the specific portion visible for each tooth and gum area examined.

19. The method according to claim 16 including bending said tip around tortuous pockets.

20. The method according to claim 16 including locating furcation involvement.

21. The method of claim 16 including eliciting any bleeding while probing to diagnose gingivitis.

22. The method of claim 16 including bending the tip around corners in tortuous pockets.

23. The method of clam 16 including bending the tip into furcations to diagnose furcation involvement.

24. A dental probe, comprising:
 (a) an elongated member having a proximal end and a distal end;
 (b) said elongated member being an approximately 40% talcum filled plastic, wherein the plastic is selected from a group consisting of polypropylene and polybutylene terephthalate;
 (c) said distal end having a tip thereon and being flexible, generally cylindrical and tapered to the tip;
 (d) said distal end further comprising a first portion indicating a non-diseased condition and a second portion indicating a diseased condition, at least one of said first and second portions having a color code contrasting to the other portion;
 (e) said first portion being disposed between the tip and the second portion, and said second portion being disposed adjacent said first portion.

* * * * *